United States Patent [19]

Castaldi et al.

[11] Patent Number: 4,764,641

[45] Date of Patent: Aug. 16, 1988

[54] PROCESS FOR PREPARING OPTICALLY ACTIVE CARBONYL COMPOUNDS

[75] Inventors: Graziano Castaldi, Briona; Silvia Cavicchioli, Costermano; Claudio Giordano, Vicenza; Carlo Restelli, Gerenzano, all of Italy

[73] Assignee: Zambon Spa., Vicenza, Italy

[21] Appl. No.: 915,518

[22] Filed: Oct. 6, 1986

[30] Foreign Application Priority Data

Oct. 4, 1985 [IT] Italy ................ 22357 A/85

[51] Int. Cl.$^4$ .................................. C07C 45/55
[52] U.S. Cl. .................... 568/319; 568/355; 568/386; 568/483; 568/447; 549/450; 549/452
[58] Field of Search ........... 549/450, 452; 568/319, 568/355, 386, 483, 442

[56] References Cited

FOREIGN PATENT DOCUMENTS

| 0086430 | 9/1981 | European Pat. Off. ............ 568/319 |
| 0087807 | 9/1983 | European Pat. Off. ............ 549/450 |
| 0158255 | 4/1985 | European Pat. Off. ............ 568/319 |
| 0158915 | 10/1985 | European Pat. Off. ............ 549/450 |

OTHER PUBLICATIONS

Chemical Abstracts: vol. 81, 1974; p. 3205.
Chemical Abstracts; vol. 104, 1986, p. 207184.
Chemical Abstracts, vol. 101, 1984, p. 211020.

*Primary Examiner*—James H. Reamer
*Attorney, Agent, or Firm*—Cushman, Darby & Cushman

[57] ABSTRACT

A process is described for preparing optically active alpha-halogenated carbonyl compounds.

This process consists of transforming the carbonyl compound into the corresponding acetal with tartaric acid or a derivative thereof, halogenating this acetal and releasing the carbonyl compound.

19 Claims, No Drawings

PROCESS FOR PREPARING OPTICALLY ACTIVE CARBONYL COMPOUNDS

This invention relates to a process for preparing optically active alpha-functionalised carbonyl compounds, and more particularly relates to a process for preparing optically active alpha-halogenated carbonyl compounds by distereoselective halogenation of optically active acetals followed by release of the carbonyl group. Optically active alpha-functionalised carbonyl compounds (in particular aldehydes and ketones) are important intermediates in organic synthesis.

To our knowledge, only a few processes of limited interest and of little industrial application are known, and these only for the synthesis of specific optically active alpha-functionalised ketones.

European patent application No. 81993 (Syntex) describes the synthesis of alpha-haloethyl-aryl-ketones consisting of a coupling of Friedel-Crafts reaction between an aromatic compound and an optically active alpha-bromo-propionyl-bromide.

This latter, which is itself prepared from lactic acid and alanine, racemises at temperatures exceeding $-10°$ C. [J. Am. Chem. Soc., 76, 6054, (1954)], making implementation of the process on an industrial scale difficult.

In any event, the scope of the process described in the aforesaid European patent application appears of limited interest and is certainly not generalisable.

Another particular case is described in the work published in Chem. Pharm. Bull. 21, 54 (1973) regarding the halogenation of cyclic ketones in the form of enamines of N-proline esters. The process leads to optically active cyclic ketones with low enantiomeric excesses, and appears limited to cyclohexanone and cycloheptanone as substrates.

In this respect, halogenating the cyclopentanone enamine leads to a raceme product.

The present invention provides an economical process of simple industrial application, which enables optically active alphahalogenated carbonyl compounds (aldehydes, ketones) to be obtained in a very general manner.

Said process consists of transforming the carbonyl compound into the corresponding acetal of L(+) or D(−)-tartaric acid or their derivatives, subjecting this acetal to halogenation, and then releasing the carbonyl group.

The process can be applied to a large number of substrates, the only requirement being that a prochiral group exists in the alpha position at the carbonyl group.

By way purely of example and without limiting the scope of the invention thereby, the carbonyl substrates which can be used in the process according to the present invention can be represented by the following formula:

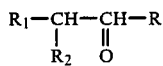   (I)

in which

R represents a hydrogen atom (I=aldehyde), an alkyl, a cycloalkyl, an aryl or an arylalkyl, all these groups possibly being substituted (I=ketone);

$R_1$ represents an alkyl, a cycloalkyl or an aryl, possibly substituted;

$R_2$ represents a hydrogen atom or, together with $R_1$, constitutes a substituted pentamethylene chain which together with the carbon atom to which $R_1$ and $R_2$ are bonded forms a cyclohexyl substituted or orthocondensed with an aromatic group which can itself be substituted;

or R and $R_1$ together consitute a methylenic chain, possibly substituted (I=cyclic ketone).

Specific examples of the aforesaid substituents are, in the case of alkyl: methyl, ethyl, n.propyl, i.propyl, n.butyl, t.butyl, n.pentyl etc., the length of the chain and the presence of any branches having no influence on the process according to the invention; in the case of cycloalkyl: cyclopropyl, cyclobutyl, cyclopentyl, cyclohexyl etc.; in the case of arylalkyl: benzyl, furylmethyl, pyridylmethyl, phenylmethyl, naphthylmethyl etc.; in the case of aryl: aromatic and heteroaromatic radicals such as phenyl; for cyclohexyl orthocondensed with an aromatic group: tetrahydronaphthyl or the group of formula

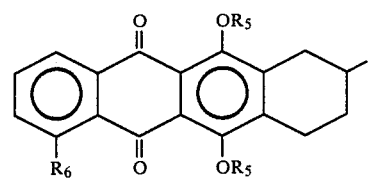

in which $R_5$ represents a hydrogen atom, a methy or acetyl and $R_5$ represents a hydrogen atom, a hydroxyl or methoxy.

All the aforesaid groups can be substituted with atoms or groups compatible with the reactions involved in the process. Examples of possible substituents are halogen atoms, aryls, alkyls, alkoxys, alkylthio, nitro, cyano, phenoxy or other groups.

Other apparently incompatible groups can become useful according to the compounds which are to be prepared. This is the case for example of double olefinic bonds which, independently of the halogenation conditions, can interfere with this reaction and are thus incompatible.

However, in certain cases, it can be useful to obtain simultaneous halogenation of the carbonyl substrate and of any olefinic group present.

A further example consists of activated aromatic groups which can be halogenated during the reaction.

In any event, whenever required, the aromatic halogen atom can be easily removed by hydrogenolysis.

As stated heretofore, the first step of the process consists of transforming the carbonyl compound into the corresponding acetal by reaction with L(+) or D(−)-tartaric acid or their derivatives.

This reaction is a normal acetalation reaction which is implemented by conventional techniques, for example in the presence of a dehydrating agent such as an orthoformate or by azeotropic distillation. Alternatively, the reaction can be implemented by trans-acetalation.

The acetalation reaction preferably uses diesters of L(+) or (D(−)-tartaric acid. In this manner a 2,4,5-trisubstituted or 2,2,4,5-tetrasubstituted 1,3-dioxolane is obtained in which the two alkoxycarbonyl groups of the tartaric diester are in position 4 and 5. These groups can be changed into carboxyl or aminocarboxyl groups by simple reactions. The carbon atoms in position 4 and 5 of the dioxolane ring have both R configuration if L(+) tartaric acid or its derivatives are used as the starting substance, and have both S configuration if D(−)-tartaric acid or its derivatives are used.

Considering the compounds of formula I as representative of the carbonyl compounds which can be used in the process according to the present invention, their acetalation in accordance with the aforesaid leads to the formation of compounds of formula:

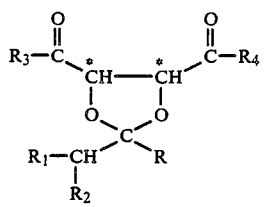
(II)

in which $R_3$ and $R_4$ independently represent a hydroxyl, alkoxy, an amino group possibly mono or dialkyl-substituted or a O—M+ group where M+ is the cation of an alkaline metal; the carbon atoms marked with an asterisk both have R or S configuration; the substituents R, $R_1$ and $R_2$ have the meanings given for formula I.

Halogenation of the compounds of formula II leads to the corresponding alpha-halogenated compounds of formula:

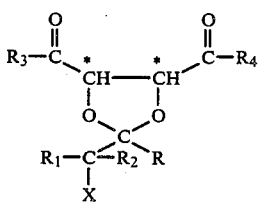
(III)

in which R, $R_1$, $R_2$, $R_3$ and $R_4$ have the aforesaid meanings and X represents a chlorine, bromine or iodine atom.

Surprisingly, from this reaction compounds of formula III are obtained in which there prevails one of the two diastereoisomers with reference to the new centre of asymmetry constituted by the carbon atom carrying the substituent X (hereinafter this centre of asymmetry will be indicated by c).

The predominant configuration (R or S) of the centre of asymmetry c is a function of the configuration of the carbon atoms in position 4 and 5 of the dioxolane ring in the compounds of formula II.

In this respect, if a compound of formula II in which the carbon atoms marked with an asterisk both have R configuration [acetal of L(+)-tartaric acid or a derivative thereof] is halogenated, the corresponding compound of formula III is obtained in which one of the two diastereoisomers, for example the diastereoisomer in which the centre of asymmetry c has S configuration, prevails.

If however the same compound of formula III is to be prepared in which the diastereoisomer with its centre of asymmetry c in R configuration prevails, it is necessary only to halogenate the acetal of the same carbonyl compound with D(−)-tartaric acid or a derivative thereof, ie halogenate the analogous compound of formula II in which both the carbon atoms marked with an asterisk have S configuration.

Obviously the R or S configuration of the centre of asymmetry c is not an absolute configuration, but depends on nomenclature rules and can therefore vary according to the meanings of $R_1$ and $R_2$.

The halogenation reaction is conducted by treating the compound II with a suitable halogenating agent in an inert solvent at a temperature of between −30° and +50° C., but preferably between −10° C. and ambient temperature.

The halogenating agents useful in the process according to the invention are known halogenating agents such as bromine ($Br_2$), ammonium, pyridein, pyrrolidein or phosphonium perbromides, cupric bromide, sulphuryl chloride, perchloryl chlorofluoride ($FClO_3$), hexachloro-cyclohexadienone, N-bromosuccinimide, iodine chloride etc.

From the point of view of economy combined with high diastereoisomeric excess obtainable, the preferred halogenating agent is bromine.

All solvents which are inert under reaction conditions and able to ensure at least partial solubility of the reagents are in principle suitable as the reaction environment for the aforesaid halogenation.

In practice, those which have been found particularly useful are aliphatic hydrocarbons, chlorinated hydrocarbons such as $CHCl_3$, $CH_2Cl—CH_2Cl$, $CHCl_2—CH_3$, $CH_2Cl_2$, tetrahydrofuran, acetonitrile, benzene, toluene, chlorobenzene, ortho-dichlorobenzene, acetic acid, carbon disulphide, sulpholane, ethyl acetate, and ethylene glycol dimethylether.

It is important to note that the diastereoisomer compounds of formula III can be easily separated by known techniques, for example chromatographic techniques, to thus obtain the single diastereoisomer in pure form.

In the fairly frequent case in which halogenation leads to a large diastereoisomeric excess, crystallisation is sufficient to obtain the predominant diastereoisomer in pure form.

It has also been noted that in some cases halogenating compound II leads not only to compounds III but also to the corresponding compounds of formula:

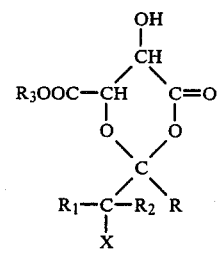
(III-A)

(in which R, $R_1$, $R_2$, $R_3$ and X have the aforesaid meanings). This occurs in particular when using bromine to brominate compounds of formula II in which $R_4$ is a hydroxyl.

The compounds of formula III-A, which have no precedent in the literature, behave in an identical manner to the compounds III in the process according to the present invention, and thus the term "compounds of formula III" will hereinafter also include the corresponding compounds of formula III-A.

In the case of symmetrical ketones (R=$R_1$—CH—$R_2$), halogenation leads to the monobromo derivative or the dibromo derivative, depending on the reaction conditions and reagent used.

It is important to note that the second bromine atom also enters in a diastereoselective manner.

The compounds of formula II and III in which R represents a possibly substituted aryl, $R_1$ a non-substituted $C_1-C_4$ alkyl and consequently $R_2$ a hydrogen atom, the preparation of these compounds and their use in the synthesis of optically active alpha-arylakanoic acids by rearrangement, have already been described in the copending Italian patent applications No. 7204 A/84, 7206 A/84 and 7207 A/84 in the name of the present applicant.

The important results of the diastereoselective halogenation of the compounds II would not in any way be useful for the purposes of preparing optically active alpha-functionalised carbonyl compounds if the release of these compounds from the acetal group, ie hydrolysis of the compound III, had a racemising effect or had to take place in a racemising environment for the carbonyl compound obtained.

The normal conditions for acetal hydrolysis (water and acid pH) have proved unsuitable as hydrolysis requires drastic conditions and gives rise to undesirable by-products and racemisation of any carbonyl compound formed.

In contrast, when the compounds III are treated with a strong aicd in substantially anhydrous environment, possibly in the presence of a suitable inert solvent, compounds of formula;

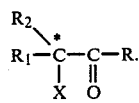

are obtained (in which R, $R_1$, $R_2$ and X have the aforesaid meanings but with the exclusion of those compounds in which $R_1$ is a non-substituted alkyl when R is a possibly substituted aryl, in that the preparation of these compounds is described in the copending patent application in the name of the present applicant entitled "process for preparing optically active alpha-haloalkylaryl-ketones" filed on the same date) in which the enantiomeric excess reflects the diastereoisomeric excess of the starting compounds.

The reaction is conducted between 0° C. and 50° C., and preferably around 10°-15° C.

Suitable strong acids are methanesulphonic, sulphuric, p.toluenesulphonic, fluorosulphonic, trifluoromethanesulphonic acid and generally those strong acids available in substantially anhydrous form.

To obtain acceptable reaction rates, an acid excess of around 3-10 times the compound of formula I by weight is used.

Depending on the nature of the substrate, it can be useful to use an organic solvent to optimise the results.

In all cases the organic solvent is used in small quantities, around 10-30% of the acid by weight.

Suitable solvents are lower alcohols, chlorinated hydrocarbons such as 1,2-dichloroethane nd methylene chloride, or their mixtures.

As stated heretofore the compounds of formula IV are useful intermediates in organic synthesis.

Their uses include the preparation of enantiomerically pure epoxides by stereospecific reduction of the carbonyl group to alcohol, converting the halohydrin thus obtained into epoxide and reacting with organometallic reagents to form optically pure 1, 1-disubstituted epoxides.

The halogen atom of the compounds IV can also be substituted in a stereospecific manner with nucleophilic reagents to form a very wide range of optically active alpha-functionalised carbonyl compounds.

In a specific embodiment, the present invention relates to a process for preparing compounds of formula:

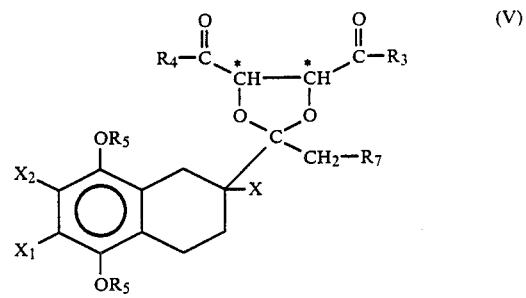

in which $R_3$, $R_4$, $R_5$ and X have the aforesaid meanings; $R_7$ represents a hydrogen atom or a chlorine, bromine or iodine atom; $X_1$ and $X_2$ represent a hydrogen or together constitute the group

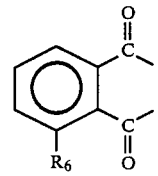

in which $R_6$ has the aforesaid meanings.

The compounds of formula V are intermediates in the synthesis of tetracycline antibiotics of antineoplastic activity, and more specifically are intermediates in the preparation of the aglycones of said compounds.

This class of compound includes the drugs known by the name of carubicin, daunorubicin, doxorubicin ["USAN and the USP Dictionary of Drug Names", USP Convention Inc.—Rockville Md-USA (1981) pages 74, 112, 135] and 4-demethoxy-daunorubicin [Chim. Ind., 65, 359, (1983)]

The aglycones of these compounds have in common the tetracyclic skeleton of formula

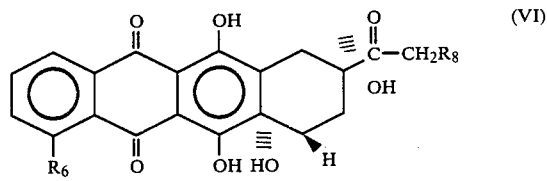

Carubicin aglycone: I, $R_6$=OH, $R_8$=H
Daunorubicin aglycone: I, $R_6$=OCH$_3$, $R_8$=H
Doxorubicin aglycone: I, $R_6$=OCH$_8$, $R_8$=OH
4-demethoxy-daunorubicin aglycone: I, $R_6$=H, $R_8$=H.

By nomenclature conventions, the positions of the tetracyclic nucleus VI are indicated by the following numbering:

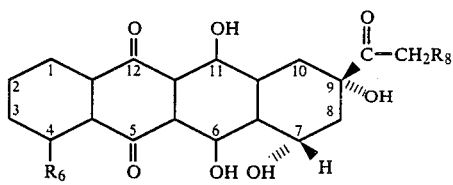

Of the most recent processes (aforesaid Chim. Ind.) for the synthesis of the compounds of formula VI, the important ones comprise as their last step the hydroxylation of the corresponding 7-desoxy derivative of formula

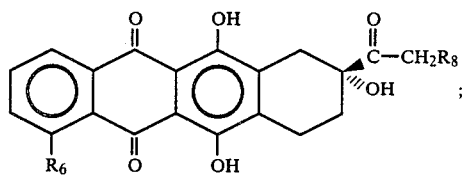

in which $R_6$ and $R_8$ have the aforesaid meanings.

A useful method for the synthesis of compound VII comprises a Friedel-Crafts reaction between a phthalic anhydride of formula

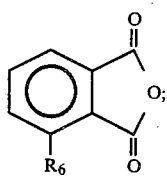

and the tetrahydronaphthalene derivative of formula

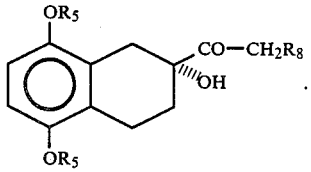

An essential requirement from the biological viewpoint is that the stereochemistry of the carbon atom in position 9 corresponds to the carbon atom carrying the acetyl group in the compounds of formula IX.

For this reason, various resolution systems at the level of compound IX or compound VII have been studied (for example European patent application No. 87807, Sumitomo Chemical Company).

The process according to the present invention enables compounds of formula V to be obtained in which the substituent X (halogen atom) is introduced in a diastereoselective manner. The compounds of formula V form the compounds of formula VII enantioselectively by simple steps.

These steps for transforming compounds V into compounds VII are known or in any event easily implemented, and comprise, not necessarily in the indicated order, a) substituting the halogen atom X or, if appropriate, both the halogen atoms X and $R_7$ with a hydroxyl, b) releasing the carbonyl from the ketalising group (tartaric acid derivative) and possibly c) a Friedel-Crafts reaction with the phthalic anhydride VIII of the compound V when $X_1$ and $X_2$ are hydrogen atoms in this latter.

Because of the fact that, in the specific embodiment considered, the process according to the invention can be implemented either on bicyclic or tetracyclic compounds, the starting compound is indicated by the following formula

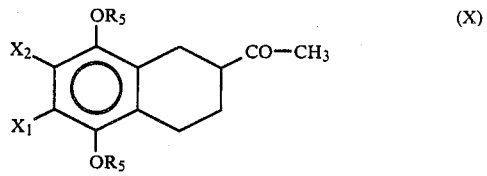

in which $R_5$ is a hydroxyl protector group, in particular methyl or acetyl; $X_1$ and $X_2$ are hydrogen atoms, or $X_1$ and $X_Y$ together constitute the group

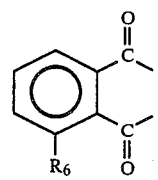

The process according to the present invention comprises the following steps:

(1) Ketalisation of a compound of formula X with L(+) or D(−)-tartaric acid or a derivative thereof to obtain a compound of formula:

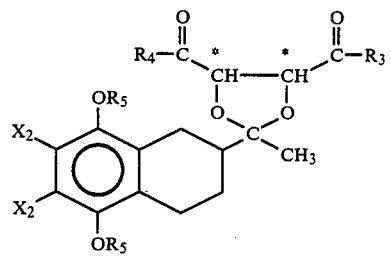

in which $R_3$, $R_4$, $R_5$, $X_1$ and $X_2$ have the aforesaid meanings; the carbon atoms marked with an asterisk having both R or S configuration.

(2) Reacting a compound of formula XI with a halogenating agent to diastereoselectively obtain a compound of formula

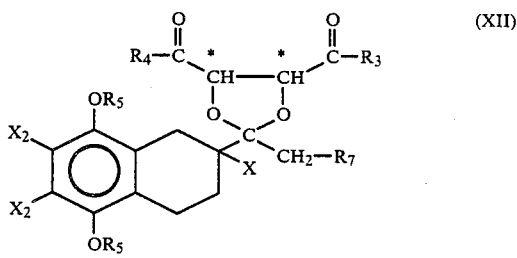

in which $R_3$, $R_4$, $R_5$, $X_1$ and $X_2$ have the aforedescribed meanings, X represents a chlorine, bromine or iodine atom, $R_7$ represents a hydrogen atom or is equal to X.

The compounds of formula XII in which $R_7=H$ are obtained by reacting the compound XI with a substantially equimolar quantity of the halogenating agent; those in which $R_7$ is equal to X and represents a chlorine, bromine or iodine atom are obtained by reacting the compound XI with a bimolar quantity of the halogenating agent.

If required, it is possible to convert the dihalo-derivative (X and $R_7$=Cl, Br, I) into the monohalo-derivative by hydrogenolysis of the —$CH_2R_7$ group into $CH_3$.

Bromination of the compounds of formula XI in which $R_3$ and/or $R_4$ represent a hydroxyl can lead to the formation of compounds of formula

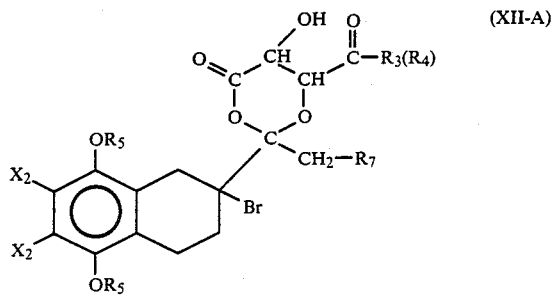

(XII-A)

which in the subsequent reactions behave as the compounds of formula XII.

The third stage of the process according to the present invention, ie releasing the carbonyl from the ketalising group, can be conducted directly on the compound of formula XII or XII-A.

However, for preparing the precursors (VII) of the aglicones VI it can be convenient to release the carbonyl group after substituting the halogen atom or, if appropriate, both the halogen atoms of the compounds XII or XII-A with the hydroxyl and, if $X_1$ and $X_2$ in the compounds XII are hydrogen atoms, condensing with the phthalic anhydride VIII.

Operating in this manner, the compounds of formula XII are subjected to the following reactions.

(3) Substituting the halogen atom (X) or, if appropriate, both the halogen atoms (X and $R_7$) in the compound of formula XII with a hydroxyl to obtain a compound of formula

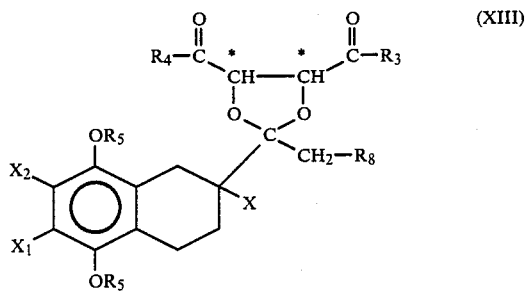

(XIII)

in which $R_3$, $R_4$, $R_5$, $X_1$ and $X_2$ have the aforesaid meanings and $R_8$ represents a hydrogen atom if $R_7$=H in the corresponding compound of formula XII, or represents a hydroxyl if $R_7$ is a halogen atom in the compound of formula XII.

(4) Condensing the compound of formula XIII, if $X_1$ and $X_2$ are hydrogen atoms, with a phthalic anhydride of formula VIII to obtain a compound of formula

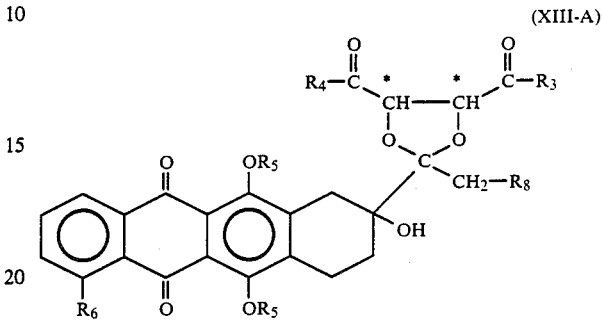

(XIII-A)

in which $R_3$, $R_4$, $R_5$, $R_6$ and $R_8$ have the aforesaid meanings, and in particular $R_5$ is a hydrogen atom.

Obviously, stage 4 is not implemented if the compound of formula XIII is already tetracyclic, ie if $X_1$ and $X_2$ represent the group

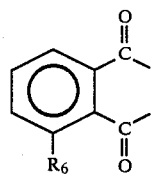

In this case, the compound XIII is already the compound XIII-A.

Condensation with the phthalic anhydride VIII can be also conducted on the other intermediates of formula XI and XII if $X_1$ and $X_2$ are hydrogen atoms, to obtain the corresponding compounds of formula XI and XII in which $X_1$ and $X_2$ represent the residue of the phthalic anhydride of formula VIII.

Depending on the experimental conditions, condensation with phthalic anhydride can simultaneously lead to the release of the hydroxyls in position 6 and 11 of the tetracyclic nucleus, to form compounds of formula XIII in which $R_5$=H.

(5) Releasing the carbonyl of the compound XIII-A from the ketalising agent to obtain the corresponding compound of formula VII.

The process according to the present invention, in the specific embodiment considered, can be represented by the reactions shown in the following scheme 1.

SCHEME 1

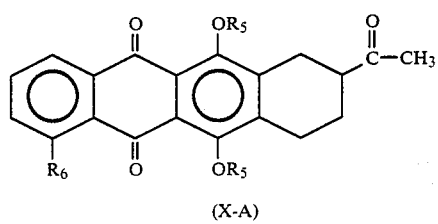

(X-A)

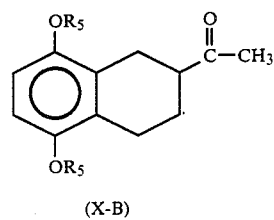

(X-B)

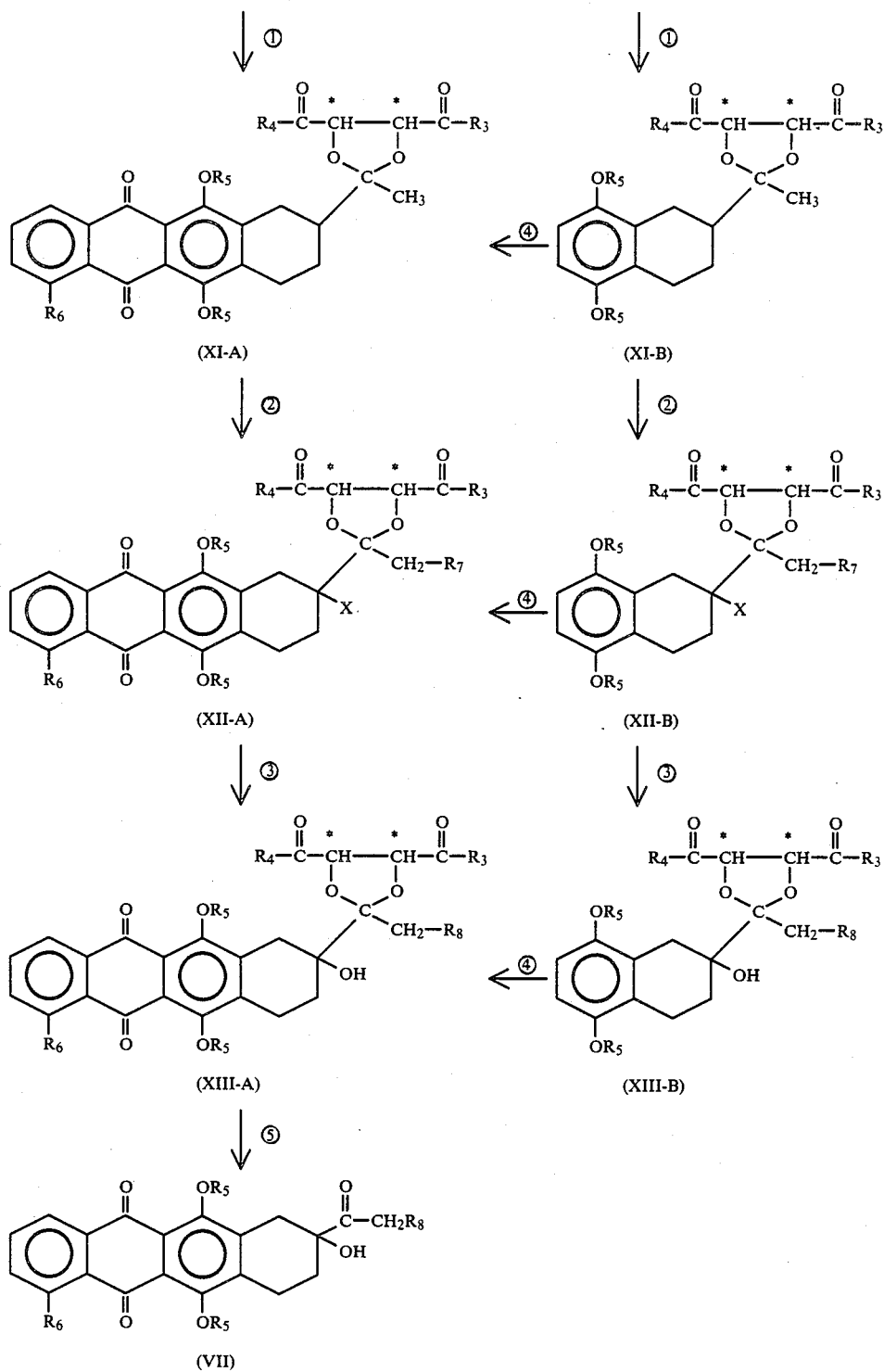

In Scheme 1, the substituents $R_3$, $R_4$, $R_5$, $R_6$, $R_7$ and $R_8$ have the aforesaid meanings; the compounds X-B, XI-B, XII-B and XIII-B are the aforesaid compounds of formula X, XI, XII and XIII respectively, in which $X_1$ and $X_2$ are hydrogen atoms; the compounds X-A, XI-A, XII-A and XIII-A are the aforesaid compounds X, XI, XII and XIII respectively, in which $X_1$ and $X_2$ together constitute the group

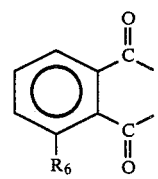

Finally, the arrow numbers on Scheme 1 indicate the aforesaid process stages.

The practical implementation of the process is simple, requires very easily obtainable low-cost reagents, can be carried out on an industrial scale without problems and, a still more important aspect, selectively provides the compounds of formula VII in which the carbon atom in position 9 is of R configuration, ie the configuration required for antitumoral activity in tetracycline antibiotics.

The process is also versatile because it enables compounds of formula VII to be prepared in which $R_8$ is either a hydrogen atom or a hydroxyl, ie the precursors of two different sub-classes of tetracycline antibiotic.

In practical terms, the various process stages are conducted in the following manner:

STAGE 1

The reaction between the compound X and L(+) or D(−)-tartaric acid or a derivative thereof is conducted as described for ketalisation of the compounds I, for example in the presence of a trialkylorthoformate or another dehydrating agent, or by azeotropically distilling the water of reaction, or again by transketalisation.

This latter method, which in this case is preferred, can be conducted by reacting the dimethyl-ketal of the compound of formula V with a simple ketal of tartaric acid, for example the ketal with acetone, or alternatively it is possible to use as ketalising agent the orthoformate of formula

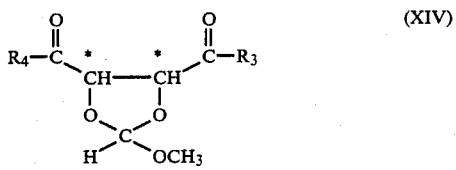

which can be easily prepared by reacting trimethylorthoformate with the suitable derivative of L(+) or D(−)-tartaric acid in the presence of a strong acid.

Generally it is preferred to use as ketalising agent a diester of L(+) or D(−)-tartaric acid to obtain the compounds of formula XI in which $R_3$ and $R_4$ represent an alkoxy. From these it is easy to prepare, if required, the other compounds of formula XI in which $R_3$ and $R_4$ represent an hydroxyl, an amino group or a O—M+ group.

These transformations are conducted by common methods of organic chemistry.

The facility to obtain different acyl derivatives (by varying $R_3$ and $R_4$) enables the solubility of the compounds of formula XI, XII and XIII to be varied within wide limits with the possibility of choosing the most suitable experimental conditions for the various substrates in conducting the subsequent stages of the process.

The carbon atoms marked with an asterisk in formula XI and the subsequent formulas both have R configuration when the ketalising agent is L(+)-tartaric acid or a derivative thereof, and both have S configuration when the ketalising agent is D(−)-tartaric acid or a derivative thereof.

STAGE 2

Halogenation of the compound XI leads to the introduction of a chlorine, bromine or iodine atom (substituent X) diastereoselectively.

This is the key which enables the compounds of formula VII to be obtained enantioselectively.

In this respect, halogenation of the compound of formula XI enables the compounds of formula XII to be obtained in which the carbon atom carrying the substituent X, which corresponds to the carbon atom is position 9 of the tetracycline nucleus, has a predetermined configuration. This configuration depends directly on the configuration of the carbon atoms marked with an asterisk in the compound of formula XI.

The halogenation reaction is conducted, analogously to that heretofore described for halogenating the compounds of formula II, by reacting the compund of formula XI with the appropriate halogenating agent in an inert solvent at a temperature of between −30° and +50° C., and preferably between −10° C. and ambient temperature.

For questions of economy and high yield, the halogenation reaction is preferably bromination, and the halogenating agent is an ammonium perbromide or bromine.

The diastereoselectivity of the halogenation reaction is very high.

STAGE 3

Stage 3 is a nucleophilic substitution of the halogen atom X or, if appropriate, of both the halogen atoms X and $R_7$, by a hydroxyl.

It is important in this stage to substitute the halogen atom X by the hydroxyl by procedures which maintain the diastereoisomeric purity of the starting compound XII.

More particularly, considering the case in which halogenation leads to the compound XII in which the carbon atom carrying the substituent X has S configuration, substituting X by the hydroxyl must lead to configuration inversion.

This result can be attained by known procedures of organic chemistry, such as the procedure described in Chem. Ber., 116, 3631, (1983).

STAGE 4

Condensing the tetrahydronaphthalene derivative of formula XI-B, XII-B or XIII-B (scheme 1) with the phthalic anhydride VIII is conducted by a normal Friedel-Crafts reaction in accordance with known procedures.

The said reaction can as a consequence have a modest racemisation which leads to compounds of formula XII-A or XIII-A (Scheme 1) in which the carbon atom in position 9 has an optical purity less than that of the corresponding compound XII-B or XIII-B respectively (Scheme 1).

The presence of the two ketalising agent carbon atoms of predetermined fixed configuration (both R or S) makes the two diastereoisomers of the compound XII-A or XIII-A easily separable by conventional methods such as fractional crystallisation or chromatographic methods.

It is therefore possible to purify the compound XII-A or, respectively, XIII-A if during the course of condensing the respective compound XII-B or XIII-B with the phthalic anhydride VIII there has been partial racemisation of the carbon atom in position 9.

More generally, it is possible to utilise the particular diastereoisomerism of the compounds XII-A, XII-B, XIII-A and XIII-B to optically separate diastereoisomers which are epimers with respect to the carbon atom carrying the substituent X or the hydroxyl respectively, each time this is necessary.

STAGE 5

Releasing the carbonyl of the compounds XIII-A from the ketalising agent is conducted as described with reference to the release of the carbonyl in the compounds of formula III.

If required, it is also possible to recover the tartaric derivative used as the ketalising agent.

The process according to the present invention therefore enables the compound II to be obtained enantioselectively with the correct isomerism in position 9.

This result is very important when considering that previously described syntheses have required a stage of isomer separation, with consequent product losses and high cost.

The following examples are described for better illustrating the invention.

EXAMPLE 1

Preparation of 2-methoxy-4(R),5(R)-dimethoxycarbonyl-1,3-dioxolane

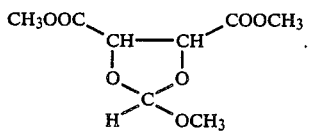

A mixture of the dimethylester of 2(R),3(R)-dihydroxybutanedioic acid (178 g; 1 mole), trimethylorthoformate (106 g; 1 mole) and methanesulphonic acid (13.5 g; 0.14 moles), kept under agitation in a nitrogen atmosphere, is heated to 100° C., distilling the volatile compounds.

After 1 hour, toluene (250 ml) is added to the reaction mixture. Trimethylorthoformate (72 g; 0.68 moles) is dropped in over 2 hours under agitation at 100° C., continuing the distillation.

The reaction mixture is then cooled to ambient temperature and poured under vigorous agitation into a 10% sodium carbonate solution (500 ml). The inorganic phase is extracted with toluene (2×250 ml). The organic extracts are washed with water (2×500 ml) and dried over sodium sulphate.

Evaporating the solvent under reduced pressure leads to 2-methoxy-4(R),5(R)-dimethoxycarbonyl-1,3-dioxolane (120 g). An analytically pure sample is obtained by chromatography in a silica gel column (eluent hexane:ether=7:3).

I.R. (neat): 1770 cm$^{-1}$ (stretching C=O).

$^1$H-NMR (CDCl$_3$—TMS) (90 MHz): delta (ppm): 3.35 (s, 3H); 3.80 (s, 6H); 4.88 (ABq, 2H, J=4.4 Hz; $\Delta v$=25.3 Hz); 5.98 (s, 1H).

EXAMPLE 2

Preparation of 2-(2-chloroethyl)-2-phenyl-4(R),5(R)-dimethoxycarbonyl-1,3-dioxolane

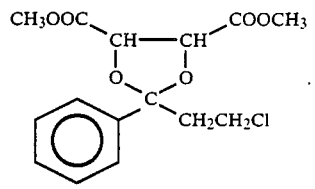

Methanesulphonic acid (0.86 g; 9.0 mmoles) is added over a period of 5 minutes to a solution of 3-chloro-1-phenyl-propan-1-one (3.36 g; 20 mmoles) and 2-methoxy-4(R),5(R)-dimethoxycarbonyl-1,3-dioxolane (8.8 g; 40 mmoles) in methylene chloride (4.5 ml), kept under agitation at +25° C. in a nitrogen atmosphere.

The reaction mixture is heated to +30°C. and kept under agitation at this temperature for 24 hours, and is then poured under vigorous agitation into a 10% sodium carbonate solution (20 ml).

After extracting with methylene chloride (2×20 ml), the pooled organic phases are dried over sodium sulphate and the solvent evaporated under reduced pressure. The residue thus obtained (8.45 g) is chromatographed in a silica gel column (eluent hexane: ethyl ether=7:3) to give 2-(2-chloroethyl)-2-phenyl-4(R),5(R)-dimethoxycarbonyl-1,3-dioxolane (3.3. g; 10 mmoles; yield 50%).

$[\alpha]_D^{20}$=23.4° (1%, CHCl$_3$).

I.R. (neat): 1760 cm$^{-1}$ (stretching C=O).

$^1$H-NMR (CDCl$_3$—TMS) (200 MHz): delta (ppm): 2.48 (m, 2H); 3.50 (s, 3H); 3.60 (dd, 2H, J$_{syn}$=7.2 Hz; J$_{anti}$=9.0 Hz); 3.83 (s, 3H); 4.88 (ABq, 2H, J=5.6 Hz; $\Delta v$=16.0 Hz); 7.30–7.46 (m, 5H).

EXAMPLE 3

Preparation of the diastereoisomer mixture of 2-(1-bromo-2-chloroethyl)-2-phenyl-4(R),5(R)-dimethoxycarbonyl-1,3-dioxolane

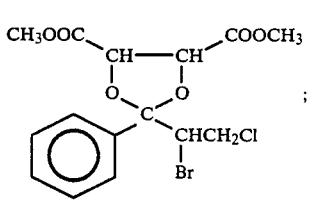

A solution of bromine (0.93 g; 5.8 mmoles) in carbon tetrachloride (1.0 ml) is added over 5 minutes to a solution of 2-(2-chloroethyl)-2-phenyl-4(R),5(R)-dimethoxycarbonyl-1,3-dioxolane (1.64 g; 5 mmoles) and 2-methoxynaphthalene (79 mg; 0.5 mmoles) in carbon tetrachloride (10 ml) kept under agitation in a nitrogen atmosphere at +15° C.

The reaction mixture is kept at +15° C. for 6.5 hours, and is then poured under agitation into a 10% sodium carbonate solution (50 ml). The aqueous phase is extracted with methylene chloride (2×25 ml). The organic extractors are washed with water (2×25 ml), dried over sodium sulphate and concentrated under reduced pressure.

The residue thus obtained (1.96 g) is chromatographed in a silica gel column (eluent hexane: ethyl ether=70:30).

2-(1-bromo-2-chloroethyl)-2-phenyl-4(R),5(R)-dimethoxycarbonyl-1,3-dioxolane (1.68 g; 4.1 mmoles; yield 82.5%) is obtained as a mixture of diastereoisomers 1 and 2 in the ratio 1:2=70:30, determined by HPLC analysis and confirmed by $^1$H-NMR (200 MHz) analysis.

Diastereoisomer 1 (predominant): delta (ppm): 3.56 (s, 3H); 3.82 (ABX, 2H, $J_{ACHBr}$=3.0 Hz, $J_{BCHBr}$9.7 Hz, $J_{gem}$=12.2 Hz, $\Delta v$=77.7 Hz); 3.84 (s, 3H); 4.42 (dd, 1H, $J_{ACHBr}$=3.0 Hz, $J_{BCHBr}$=9.7 HZ); 4.89 (ABq, 2H, J=6.0 Hz, $\Delta v$=21.9 Hz); 7.37–7.55 (m, 5H).

Diastereoisomer 2 (lesser): delta (ppm); 3.55 (s, 3H); 3.81 (ABX, 2H, $J_{ACHBr}$=3.0 Hz, $J_{BCHBr}$=9.7 Hz, $J_{gem}$=12.2 Hz, $\Delta v$=77.7 Hz); 3.84 (s, 3H); 4.45 (dd, 1H, $J_{ACHBr}$=3.0 Hz, $J_{BCHBr}$=9.7 HZ); 4.88 (ABq, 2H, J=6.0 Hz, $\Delta v$=15.6 Hz); 7.37–7.55 (m, 5H).

EXAMPLE 4

Preparation of 2-ethyl-4(R),5(R)-dimethoxycarbonyl-1,3-dioxolane

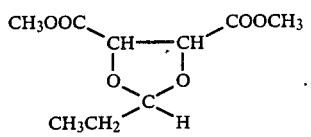

A solution of propionic aldehyde (7 g; 0.12 mmoles), dimethylester of 2(R),3(R)-dihydroxybutanedioic acid (2.14 g; 12 mmoles) and 2-methoxy-4(R),5(R)-dimethoxycarbonyl-1,3-dioxolane (39.6 g; 0.18 moles) in dichloromethane (25 ml), is cooled to +15° C. under agitation in a nitrogen atmosphere, and methanesulphonic acid (1.15 g; 12 mmoles) is added to it over 5 minutes.

The reaction mixture is kept under agitation at +15° C. for 24 hours, and is then poured under agitation into a 10% sodium carbonate solution (100 ml). The inorganic phase is extracted with methylene chloride (2×50 ml) and the organic extracts are washed with water (2×100 ml) and dried over sodium sulphate. After evaporating the solvent under reduced pressure, a residue is obtained (20.6 g) from which, after chromatography through a silica gel column (eluent haxane: ethyl ether=80.20), 2-ethyl-4(R),5(R)-dimethoxycarbonyl-1,3-dioxolane is obtained (6.1 g; 0.028 moles; yield 23%).

$[\alpha]_D^{20}$=55.2° (1%, CHCl$_3$).

I.R. (neat): 1760 cm$^{-1}$ (stretching C=O.

$^1$H-NMR (CDCl$_3$—TMS) (200 MHz): delta (ppm): 1.00 (t, 3H, J=7.6 Hz); 1.80 (dq, 2H, $J_{CH2CH3}$=7.6 Hz, $J_{CH2CH}$=4.7 Hz); 3.81 (s, 3H); 3.82 (s, 3H); 4.74 (ABq, 2H, J=4.0 Hz; $\Delta v$=25.5 Hz); 5.21 (t, 1H, J=4.7 Hz).

EXAMPLE 5

Preparation of the diastereoisomer mixture of 2-(1-bromoethyl)-4(R),5(R)-dimethoxycarbonyl-1,3-dioxolane

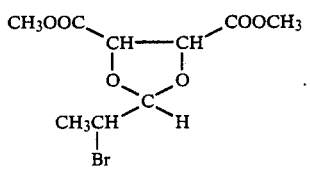

A solution of bromine (0.93 g; 5.8 mmoles) in 1,2-dichloroethane (1.0 ml) is added over 5 minutes to a solution of 2-ethyl-4(R),5(R)-dimethoxycarbonyl-1,3-dioxolane (12.1 g; 5.0 mmoles) and 2-methoxynaphthalene (79 mg; 0.5 mmoles) in 1,2-dichloroethane (15 ml), kept under agitation in a nitrogen atmosphere at +15° C.

The reaction mixture is kept at +15° C. for 48 hours, and is the processed as described in Example 3.

An impure product (1.1 g) is obtained containing the mixture of diastereoisomers 3 and 4 of 2-(1-bromoethyl)-4(R),5(R)-dimethoxycarbonyl-1,3-dioxolane in the ratio 3:4=62:38, determined by 1H-NMR (200 MHz) analysis. An analytically pure sample (0.35 g) is obtained by chromatography in a silica gel column (eluent hexane: acetone=9:1).

$^1$H-NMR (CDCl$_3$—TMS) (200 MHz): Diastereoisomer 3 (predominant): delta (ppm): 1.68 (d, 3H, J=6.8 Hz); 3.78 (s, 3H); 3.79 (s, 3H); 4.09 (dq, 1H, $J_{CHCH3}$=6.8 Hz, $J_{CHCH}$=5.3 Hz); 4.81 (ABq, 2H, J=3.4 Hz, $\Delta v$=27.8 Hz); 5.33 (d, 1H, J=5.3 Hz).

Diastereoisomer 4 (lesser): delta (ppm): 1.70 (d, 3H, J=6.8 Hz); 3.73 (s, 3H); 3.77 (s, 3H); 4.09 (dq, 1H, $J_{CHCH3}$=6.8 Hz, $J_{CHCH}$=5.3 Hz); 4.81 (ABq, 2H, J=3.4 Hz, $\Delta v$=27.8 Hz); 5.33 (d, 1H, J=5.3 Hz).

EXAMPLE 6

Preparation of 2,2-diethyl-4(R),5(R)-dimethoxycarbonyl-1,3-dioxolane

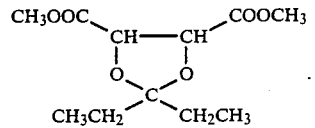

A mixture of 3-pentanone (21.5 g; 0.25 moles), dimethylester of 2(R),3(R)-dihydroxybutanedioic acid (53.0 g; 0.30 moles) and trimethylorthoformate (29.0 g; 0.27 moles) is heated to +45° C. under agitation in a nitrogen atmosphere.

Methanesulphonic acid (1.44 g; 15 mmoles) is added over 5 minutes to the solution thus obtained, which is then heated to +60° C.

After 1.5 hours the reaction mixture is cooled to ambient temperature and processed as described in Example 4.

The residue thus obtained (48.5 g) is chromatographed in a silica gel column to provide 2,2-diethyl-4(R),5(R)-dimethoxycarbonyl-1,3-dioxolane 46.1 g; 0.19 moles; yield 75.6%).

$[\alpha]_D^{20}$=19.4° (1%, CHCl$_3$).

I.R. (neat): 1780 cm$^{-1}$ (stretching C=O).

$^1$H-NMR (CDCl$_3$—TMS) (200 MHz): delta (ppm): 0.92 (t, 6H, J=7.4 Hz); 1.71 (q, 4H, J=7.4 Hz); 3.81 (s, 6H); 4.73 (s, 2H).

EXAMPLE 7

Preparation of the diastereoisomer mixture of 2-(1-bromoethyl)-2-ethyl-4(R),5(R)-dimethoxycarbonyl-1,3-dioxolane

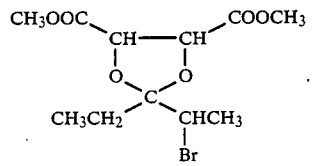

A solution of bromine (1.85 g; 11.6 mmoles) in carbon tetrachloride (3.7 ml) is added over 5 minutes, after cooling to −10° C., to a solution of 2,2-diethyl- 4(R),5(R)-dimethoxycarbonyl-1,3-dioxolane (4.5 g; 18.4 mmoles) and 2-methoxynaphthalene (0.29 g; 1.84 mmoles) in carbon tetrachloride (37 ml), cooled to $-10°$ C. and kept under agitation in nitrogen atmosphere.

The reaction mixture is left under agitation at $-10°$ C. for 3 hours and is the poured under agitation into a 10% sodium carbonate solution (100 ml). After extracting the aqueous phase with methylene chloride (2×50 ml), the organic extracts are dried over sodium sulphate and the solvent is evaporated under reduced pressure.

An impure product is obtained (4.4 g) in which the 2-(1-bromoethyl)-2-ethyl-4(R),5(R)-dimethoxycarbonyl-1,3-dioxolane is present as a mixture of diastereoisomers 5 and 6 in the ratio 5:6=86:14, determined by $^1$H-NMR (200 MHz) analysis. An analytically pure sample is obtained by chromatography in a silica gel column (eluent hexane: acetone=95:5).

$^1$H-NMR (CDCl$_3$—TMS) (200 MHz): Diastereoisomer 5 (predominant): delta (ppm): 0.94 (t, 3H, J=7.4 Hz); 1.69 (d, 3H, J=6.9 Hz); 1.95 (ABX$_3$, 2H, J$_{AB}$=14.7 Hz, J$_{CH2CH3}$=7.4 Hz, Δv=57.9 Hz); 3.80 (s, 3H); 3.82 (s, 3H); 4.19 (q, 1H, J=6.9 Hz); 4.82 (ABq, 2H, J=7.1 Hz, Δv=18.2 Hz).

Diastereoisomer 6 (lesser): delta (ppm): 0.94 (t, 3H, J=7.4 Hz); 1.70 (d, 3H, J=6.9 Hz); 1.95 (ABX$_3$, 2H, J$_{AB}$=14.7 Hz, J$_{CH2CH3}$=7.4 Hz, Δv=57.9 Hz); 3.80 (s, 3H); 3.82 (s, 3H); 4.20 (q, 1H, J=6.9 Hz); 4.79 ABq, 2H, J=7.1 Hz, Δv=20.8 Hz).

EXAMPLE 8

Preparation of 2,2-di-(1-bromoethyl)-4(R),5(R)-dimethoxycarbonyl-1,3-dioxolane

A solution of bromine (1.76 g; 11.0 mmoles) in carbon tetrachloride (1.0 ml), is added over 5 minutes to a solution of 2,2-diethyl-4(R),5(R)-dimethoxycarbonyl-1,3-dioxolane (1.22 g; 5.0 mmoles) and 2-methoxynaphthalene (79 mg; 0.5 mmoles) in carbon tetrachloride (10 ml), kept under agitation in a nitrogen atmosphere at +15° C.

The reaction mixture is left under agitation at +15° C. for 78 hours, and is then processed as described in Example 3.

The residue thus obtained (1.5 g) is chromatographed in a silica gel column (eluent haxane: ethyl ether=70:30) to give 2,2-di-(1-bromoethyl)-4(R),5(R)-dimethoxycarbonyl1-1,3-dioxolane (0.5 g) in the form of a single diastereoisomer.

$^1$H-NMR (CDCl$_3$—TMS) (200 MHz): Diastereoisomer 7: delta (ppm): 1.72 (d, 6H, J=6.8 Hz); 3.80 (s, 3H); 3.81 (s, 3H); 4.51 (q, 2H, J=6.1 Hz); 5.05 (ABq, 2H, J=8.5 Hz, Δv=3.0).

EXAMPLE 9

A mixture of diastereoisomers 3 and 4 of 2-(1-bromoethyl)-4(R),5(R)-dimethoxycarbonyl-1,3-dioxolane prepared as described in Example 5 (0.89 g; 3 mmoles), methanesulphonic acid (0.53 ml; 6 mmoles) and dichloromethane (6 ml) is kept at ambient temperature for 4 hours. The reaction mixture is poured slowly into ice and extracted with dichloromethane. The organic phase is washed with water and with a 2% sodium bicarbonate solution, and dried with sodium sulphate.

Evaporating the solvent leaves optically active 2-bromopropionaldehyde (0.31 g).

EXAMPLE 10

Preparation of the compound 2-methyl-2-(1,4-dimethoxy-5,6,7,8-tetrahydro-6-naphthyl)-4(R),5(R)-dimethoxycarbonyl-1,3-dioxolane A mixture of 1,4-dimethoxy-6-acetyl-tetraline (234 mg, 1 mmole) prepared as described in Canadian Journal of Chemistry, 49, 2712 (1971), 2-methoxy-4(R),5(R)-dimethoxycarbonyl-1,3-dioxolane (440 mg; 2 mmoles) and methanesulphonic acid (9.6 g; 0.1 mmole) is heated under agitation to 70° C. for 2 hours.

The reaction mixture is poured into a 5% sodium bicarbonate solution and extracted with ethyl ether.

Evaporating the solvent leaves a liquid consisting mainly of the required compound.

Silica gel chromatography provides the pure product with a yield of 80%.

We claim:

1. A process for preparing optically active alpha-halogenated carbonyl compounds of formula $$R_1-\overset{*}{\underset{X}{C}}-\underset{O}{\overset{\parallel}{C}}-R. \qquad (IV)$$
$$\phantom{R_1-}\underset{\phantom{X}}{\overset{R_2}{|}}$$

in which
R represents a hydrogen atom, a possibly substituted alkyl, a possibly substituted cycloalkyl, or a possibly substituted arylalkyl;

R$_1$ represents a possibly substituted alkyl, a possibly substituted cycloalkyl, or a possibly substituted aryl;

R$_2$ represents a hydrogen atom or, together with R$_1$, constitutes a substituted pentamethylenic chain which, together with the carbon atom to which R$_1$ and R$_2$ are bonded, forms a cyclohexyl which is substituted or is orthocondensed with an aromatic group which can itself be substituted;

X represents a chlorine, bromine or iodine atom, or R and R$_1$ together constitute a possibly substituted methylenic chain; provided that when r represents a possibly substituted aryl, R$_1$ is other than a non-substituted C$_1$-C$_4$ alkyl;

said process being characterised by comprising the following steps:

(A) acetalating with L(+) of D(−)-tartaric acid or their derivatives a carbonyl compound of formula

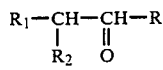  (I)

in which R and R₁ have the aforesiad meanings, to obtain a compound of formula:

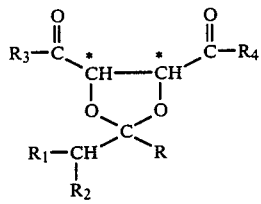

in which R, R₁ and R₂ have the aforesaid meanings, R₃ and R₄ independently represent a hydroxyl, an alkoxy, a possibly mono or di-substituted amino group, or a O—M⁺ group where M⁺ represents the cation of an alkaline metal;
the carbon atoms marked with an asterisk having both R and S configuration;

(B) halogenating a compound of formula II to diastereoselectively obtain a compound of formula:

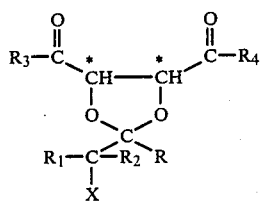

in which R, R₁, R₂, R₃ and R₄ have the aforesaid meanings and X represents a chlorine, bromine or iodine atom, and in which the carbon atom carrying the substituent X has prevalently S or R configuration;

(C) reacting compound III with a substantially anhydrous strong acid at a temperature of between 0° C. and ambient temperature.

2. A process as claimed in claim 1, wherein compound I is acetalated by reaction with a diester of L(+) or D(−)-tartaric acid.

3. A process as claimed in claim 1, wherein compound I is acetalated by trans-acetalation.

4. A process as claimed in claim 1, wherein compound II is halogenated by a halogenating agent in an inert solvent at a temperature of between −30° and +50° C.

5. A process as claimed in claim 4, wherein the halogenating agent is chosen from bromine, ammonium, pyridine, pyrrolidine or phosphonium perbromide, cupric bromide, sulphuryl chloride, perchloryl chlorofluoride, hexachloro-cyclohexadienone, N-bromosuccinimide and iodine chloride.

6. A process as claimed in claim 4, wherein the halogenating agent is bromine.

7. A process as claimed in claim 1, wherein the reaction between compound III and the strong acid is conducted in the presence of an inert solvent.

8. A process as claimed in claim 1, wherein compound III is crystallised to obtain a single diastereoisomer in pure form.

9. A process as claimed in claim 1, wherein stage (C) is conducted on a single diastereoisomer of compound III.

10. A process as claimed in claim 1, wherein the starting compound is a compound of formula

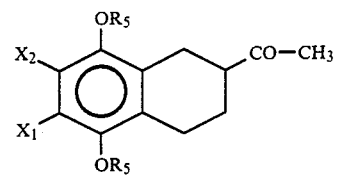

where R₅ is a hydrogen atom, a methyl or an acetyl; X₁ and X₂ represent hydrogen atoms or together consitute the group of formula

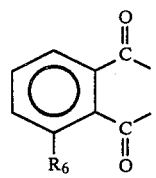

in which R₆ represents a hydrogen atom, a hydroxyl or a methoxy.

11. A process as claimed in claim 10, wherein
(A) the compound of formula X is detailed with L(+) or D(−)-tartaric acid or a derivative thereof to obtain a compound of formula:

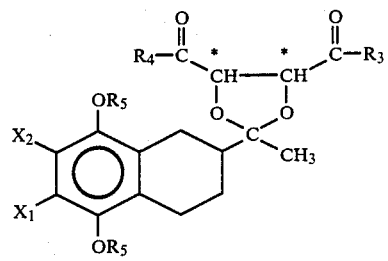

in which R₅, X₁ and X₂ have the meanings given in claim 10; R₃ and R₄, which can be the same or different, represent a hydroxyl, an alkoxy, an amino, mono or di-alkylamino group, or a O—M⁺ group where M⁺ represents the cation of an alkaline metal; the carbon atoms marked with an asterisk having both R or S configuration;

(B) the compound of formula XI is halogenated to diastereoselectively obtain a compound of formula

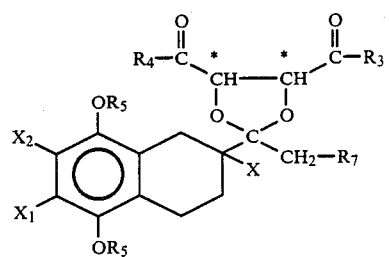

in which R₃, R₄, R₅, X₁ and X₂ have the aforesaid meanings, X represents a chlorine, bromine or iodine atom, and $R_7$ represents a hydrogen atom or is equal to X.

12. A process as claimed in claim 1 to enantioselectively obtain compounds of formula

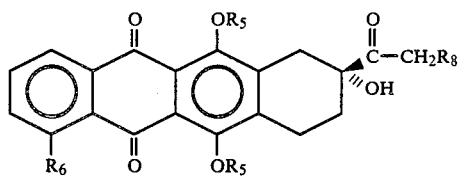

in which $R_5$ represents a hydrogen atom or a methyl, $R_6$ represents a hydrogen atom, a hydroxyl or a methoxy, $R_8$ represents a hydrogen atom or a hydroxyl; said process comprising the following steps:

(1) ketalising with L(+) or D(−)-tartaric acid or a derivative thereof a compound of formula

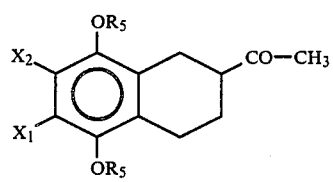

in which $R_5$ has the aforesaid meanings, $X_1$ and $X_2$ represent hydrogen atoms, and $X_1$ and $X_2$ together constitute the group

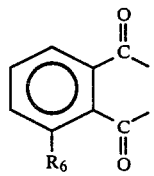

in which $R_6$ has the aforesaid meanings, to obtain a compound of formula

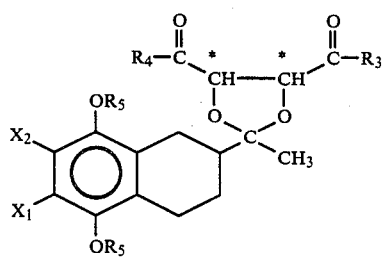

in which $X_1$, $X_2$, $R_5$ and $R_6$ have the aforesaid meanings, $R_3$ and $R_4$, which can be the same or different, represent a hydroxyl, an alkoxy, an amino, mono or dialkyl-amino group, or a O—M+ group wherein M+ represents the cation of an alkaline metal; the carbon atoms marked with an asterisk having both R and S configuration;

(2) halogenating a compound of formula XI to obtain a compound of formula

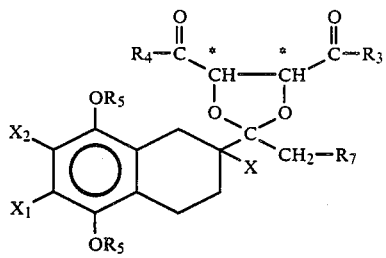

in which $X_1$, $X_2$, $R_3$, $R_4$, $R_5$ and $R_6$ have the aforesaid meanings, X represents a chlorine, bromine or iodine atom, and $R_7$ represents a hydrogen atom or is equal to X;

(3) substituting the halogen atom X and, if present, also the halogen atom $R_7$ by a hydroxyl, to obtain a compound of formula

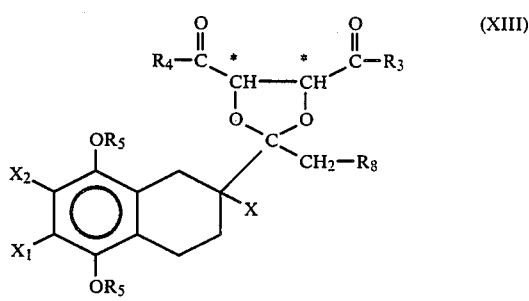

in which $X_1$, $X_2$, $R_3$, $R_4$ and $R_5$ have the aforesaid meanings and $R_8$ represents a hydrogen atom if $R_7$ is a hydrogen atom in compound XII, or represents a hydroxyl if $R_7$ is a chlorine, bromine or iodine atom in compound XII;

(4) if $X_1$ and $X_2$ represent hydrogen atoms, reacting a compound of formula XIII with a phthalic anhydride of formula

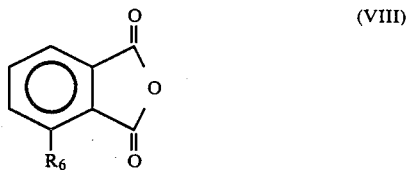

in which $R_6$ has the aforesaid meanings, to obtain a compound of formula

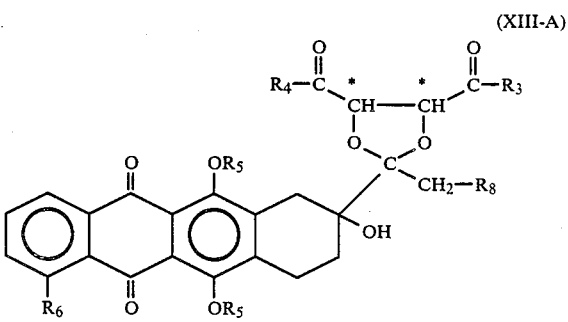

(5) releasing the carbonyl of compound XIII-A from the ketalising agent.

13. A process as claimed in claim 12, wherein stage (4) is omitted if, in the compound of formula X or XI or XII, $X_1$ and $X_2$ together constitute a group of formula

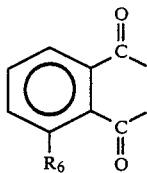

14. A process as claimed in claim 12, wherein the ketalising agent for compound X is L(+)-tartaric acid.

15. A process as claimed in claim 12, wherein the ketalising agent for compound X is a diester of L(+)-tartaric acid.

16. A process as claimed in claim 12, wherein compound XI is halogenated with a halogenating agent in an inert solvent at a temperature of between $-30°$ and $+50°$ C.

17. A process as claimed in claim 12, wherein the halogenating agent is chosen from bromine, ammonium, pyridine, pyrrolidine or phosphonium perbromide, cupric bromide, sulphuryl chloride, perchloryl chlorofluoride, hexachloro-cyclohexadienone, N-bromo-succinimide and iodine chloride.

18. A process as claimed in claim 12, wherein the halogenating agent is chosen from bromine, ammonium perbromide and N-bromo-succinimide.

19. A process as claimed in claim 12, wherein the carbonyl of compound XIII-A is released from the ketalising agent by treatment with a strong acid possibly in the presence of an inert solvent.

* * * * *